United States Patent
Rosenberg (10) Patent No.: US 7,128,719 B2
(45) Date of Patent: Oct. 31, 2006

(54) SYSTEM FOR ENHANCED CHEMICAL DEBRIDEMENT

(75) Inventor: Lior Rosenberg, Omer (IL)

(73) Assignee: Mediwound Ltd., Yavne (IL)

( * ) Notice: Subject to any disclaimer, the term of this patent is extended or adjusted under 35 U.S.C. 154(b) by 293 days.

(21) Appl. No.: 10/333,912

(22) PCT Filed: Jul. 30, 2001

(86) PCT No.: PCT/IL01/00703

§ 371 (c)(1),
(2), (4) Date: Feb. 3, 2003

(87) PCT Pub. No.: WO02/11624

PCT Pub. Date: Feb. 14, 2002

(65) Prior Publication Data

US 2003/0171675 A1    Sep. 11, 2003

(30) Foreign Application Priority Data

Aug. 3, 2000    (IL) .................................. 137689

(51) Int. Cl.
*A61N 7/00*    (2006.01)
(52) U.S. Cl. .............................. 601/2; 604/22; 604/501
(58) Field of Classification Search ............. 601/2–4; 604/22, 501; 600/439
See application file for complete search history.

(56) References Cited

U.S. PATENT DOCUMENTS

| | | | |
|---|---|---|---|
| 3,867,929 A * | 2/1975 | Joyner et al. ............... | 601/166 |
| 4,372,296 A | 2/1983 | Fahim | |
| 5,618,275 A * | 4/1997 | Bock ........................... | 604/290 |
| 5,656,015 A | 8/1997 | Young | |
| 6,478,754 B1 * | 11/2002 | Babaev ......................... | 601/2 |
| 6,500,141 B1 * | 12/2002 | Irion et al. .................... | 604/22 |
| 2003/0212350 A1* | 11/2003 | Tadlock ......................... | 601/2 |

FOREIGN PATENT DOCUMENTS

| FR | 9705695 | 11/1998 |
|---|---|---|
| WO | WO 98/32379 | 7/1998 |
| WO | WO 98/53850 | 12/1998 |

OTHER PUBLICATIONS

Klasen, HJ, "A Review on the Nonoperative Removal of Necrotic Tissue From Burn Wounds", *Burns*, 26:207-222, 2000.

* cited by examiner

*Primary Examiner*—Eleni Mantis Mercader
(74) *Attorney, Agent, or Firm*—Heslin Rothenberg Farley & Mesiti P.C.

(57) ABSTRACT

A device, system and method for enhancing the functionality and efficiency of a chemical and/or enzymatic debriding agent with a physical debriding mechanism. The debriding agent alone and the physical mechanism alone are each capable of at least some debriding activity separately, without being used in the combination. In combination, however, they are more effective, such that the debriding efficacy is increased for the combination. Preferably, the physical debriding mechanism comprises an ultrasound source.

36 Claims, 9 Drawing Sheets
(4 of 9 Drawing Sheet(s) Filed in Color)

Figure 10 - 9 days old necrotic flap

Figure 11 – After Treatment with 30' of Ultrasound & Debridase

Figure 12 - After Additional 30' Freehand Ultrasound Treatment with Debridase

Figure 13 - Clean Wound After Treatment

SYSTEM FOR ENHANCED CHEMICAL DEBRIDEMENT

This Application is a Continuation-in-Part Application of, and claims priority from, PCT Application No. PCT/IL01/00703, filed on Jul. 30 2001, and claims priority from Israeli Patent Application No. 137689, filed on Aug. 3 2000, both of which are hereby incorporated by reference as if fully set forth herein.

FIELD OF THE INVENTION

The invention is of a device, system and method for debridement of dead tissue, such as eschar or necrotic tissue, and in particular, is of such a device, system and method for potentiating the effect of a chemical and/or enzymatic debriding agent.

BACKGROUND OF THE INVENTION

Skin provides an important barrier against infectious agents such as bacteria, viruses, parasites and the like, as well as dangerous or toxic materials, and the dangerous effects of mechanical trauma, damage by ultraviolet light and the like. Damaged skin, however, may not only fail to provide such a barrier, but may itself become infected or otherwise prevent the body from heating the damaged area naturally. For certain types of injuries, such as burns or chronic wounds, for example, where the damaged tissue may be dead, it must be removed in order for the injury to heal and prevent future complications.

Therefore, for these types of injuries, a process known as "debriding" the damaged skin has been developed. The goal of the debriding process is to remove the damaged skin, with minimal or no damage to the healthy surrounding skin and also the layers of tissue below the damaged skin. The damaged skin may itself actually include dead tissue, which as used herein, includes diseased tissue, necrotic tissue and eschar. Eschar is tissue that has been damaged, burned (from thermal, chemical or electrical burn causes, for example) or from ischemia (pressure sores, diabetes or peripheral vascular disease ulcers, for example). Without debridement, bacterial infection of the dead tissue and even sepsis may occur, leading to sloughing of the damaged tissue, often with the initially undamaged tissue becoming compromised by the infection of the dead tissue. This process may lead to death of the patient. If the patient survives and recovers, the delayed healing of the damaged tissue area may cause the development of granulation tissue that eventually forms disfiguring scar tissue, which lacks flexibility as well as other physiological functions and cosmesis (appearance), which are features of healthy skin.

The eschar related complications are so important that the earliest debridement is the standard of care of any necrotic skin area. The debriding process is currently performed with physical or mechanical removal (excision) of the dead tissue, which is clearly disadvantageous because of the potential for damage to healthy tissue, both surrounding the dead tissue and also present below this tissue. For example, for surgical debridement with special knives called dermatomes, it is estimated that up to 30–50% of healthy tissue may be sacrificed during the debriding procedure. The mechanical—surgical debridement process requires a certain level of surgical skills that may not always be available. Mechanical debridement is also painful, requiring local or systemic analgesia. Therefore, the background art has focused on non-mechanical debriding processes, and also mechanical or physical processes which may be more precisely focused in order to avoid damage to healthy tissue.

For example, H. J. Klasen in "A review on the non-operative effect of necrotic tissue from burn wounds", Burns 26 (2000), 207–222, reviews non-surgical treatment of burn wounds, and describes enzymatic and chemical debriding agents, such as proteolytic enzymes and enzymes of plant origins. The review concludes that although enzymatic debridement would appear to be a useful and attractive form of treatment, it unfortunately suffers from highly variable results.

PCT Application No. WO 98/53850 also teaches the use of chemical debriding agents such as enzymes for the treatment of burned skin. However, such chemical debriding agents alone may not prove sufficiently effective for all burn or other eschar situations.

With regard to physical mechanisms for debridement, the background art includes teachings on the use of ultrasound for such debridement. For example, S. F. Schoenbach et al., in Plastic and Reconstructive Surgery, July 1980, 66(1), pp. 34–37, describe experiments performed on rats for reducing the bacterial count of infected full-thickness burn wounds by ultrasonic treatment.

PCT Application No. WO 98/32379 describes an ultrasound system for treatment of neoplastic or precancerous skin tissue. The ultrasound generating element is coupled to a container holding a liquid medium capable of transmitting ultrasound waves, which is preferably a degassed solution such as water. The solution may also contain substances that are activated by ultrasound to release free radicals. However, the use of an independently therapeutic or active solution is not taught or suggested by this reference.

Other uses of ultrasound for skin treatment have been described in French Patent Application No. 2,762,791, which discloses a probe for the simultaneous application of ultrasound and electrical current to the skin; U.S. Pat. No. 4,372,296, which describes a method of treating acne with ultrasound; and U.S. Pat. No. 5,656,015 describes an ultrasonic therapeutic system for the treatment of soft tissue. Again, these references are not focused on the removal of dead tissue.

SUMMARY OF THE INVENTION

The background art does not teach or suggest the combination of a chemical and/or enzymatic debriding agent with a physical debriding mechanism. The background art also does not teach or suggest such a combination in which each of the chemical and/or enzymatic debriding agent and the physical debriding mechanism are capable of being at least somewhat effective for debriding alone.

The present invention overcomes these deficiencies of the background art by providing a device, system and method for enhancing the functionality and efficiency of a chemical and/or enzymatic debriding agent with a physical debriding mechanism. The debriding agent alone and the physical mechanism alone are each capable of at least some debriding activity separately, without being used in the combination. In combination, however, they are synergistically more effective, such that the debriding efficacy is increased for the combination. Preferably, the physical debriding mechanism comprises an ultrasound source. More preferably, the ultrasound source comprises an ultrasound probe.

Hereinafter, the term "debriding composition" includes both chemical and enzymatic debriding agents.

The present invention also optionally and preferably comprises a container for holding an acoustic medium for enabling the ultrasound source to effectively treat the area of skin, by transmitting the ultrasound waves to the area of skin to be treated. The acoustic medium is preferably a liquid medium, but may optionally also be an acoustic gel or other semi-solid material which is capable of the cavitation phenomenon. Optionally, the acoustic medium comprises the debriding composition. Alternatively, the debriding composition may be applied separately, for example before or after treatment of the area with the ultrasound waves from the ultrasound source.

The container may optionally and preferably be constructed as an acoustic chamber or gel block, or any other container that is suitable for retaining the acoustic medium. Preferably the container allows contact between the acoustic medium and the skin, for the embodiments in which the acoustic medium also comprises the debriding composition.

The debriding composition may also optionally be formulated as a liquid, or alternatively as a gel or other semi-solid material. Illustrative examples of semi-solid materials include but are not limited to, gels, pastes, creams and the like. The debriding composition contains a debriding agent, which is preferably a chemical or enzymatic debriding agent. Illustrative examples of such agents include but are not limited to vegetable preparations including but not limited to, bromelain derivatives, including but not limited to, Debridase, Ananaim, Comosain; papain derivatives; bacterial derivative enzymes, including but not limited to, streptokinase (Varidase™), sutilains (Travase™), collagenase (Santyl™-Smith & Nephew LTD), trypsin, fibrolysin-desoxyribonuclease; chemical combinations such as Aserbin™ cream; and acids, including but not limited to, piruric, salycilic or phosphoric acids.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings, wherein.

DETAILED DESCRIPTION OF THE PREFERRED EMBODIMENTS

The present invention is of a device, system and method for enhancing the functionality and efficiency of a chemical and/or enzymatic debriding agent with a physical debriding mechanism. The debriding agent alone and the physical mechanism alone are each capable of at least some debriding activity separately, without being used in the combination. In a synergistic combination, however, they are more effective, such that the debriding efficacy is increased for the combination. Preferably, the physical debriding mechanism comprises an ultrasound source. More preferably, the ultrasound source comprises an ultrasound probe.

The ultrasound source is preferably capable of delivering ultrasound, at a frequency measured in Hz and a power measured in $W/Cm^2$, of sufficient power and frequency to be effective for treating dead tissue, in terms of having some type of debriding effect. A non-limiting example of such a sufficient power and frequency is 20 kHz and 10 $W/cm^2$; another such non-limiting example is 57 kHz and 8 $W/cm^2$. The ultrasound source is optionally and more preferably a piezo-electric ultrasound source unit.

The present invention also optionally and preferably comprises a container for holding an acoustic medium for enabling the ultrasound source to effectively treat the area of skin, by transmitting the ultrasound waves to the area of skin to be treated. The acoustic medium is preferably a liquid medium, but may optionally also be an acoustic gel or other semi-solid material. Optionally, the acoustic medium comprises the debriding composition. Alternatively, the debriding composition may be applied separately, for example before or after treatment of the area with the ultrasound waves from the ultrasound source.

The container may optionally and preferably be constructed as an acoustic chamber or gel block, or any other container that is suitable for retaining the acoustic medium. Preferably the container allows contact between the acoustic medium and the skin, for the embodiments in which the acoustic medium also comprises the debriding composition.

The debriding composition may also optionally be formulated as a liquid, or alternatively as a gel or other semi-solid material. Illustrative examples of semi-solid materials include but are not limited to, gels, pastes, creams and the like. The debriding composition contains a debriding agent, which is preferably a chemical or enzymatic debriding agent. Illustrative examples of such agents include but are not limited to, vegetable preparations including but not limited to, bromelain derivatives, including but not limited to, Debridase, Ananaim, Comosain; papain derivatives; bacterial derivative enzymes, including but not limited to, streptokinase (Varidase™), sutilains (Travase™), collagenase (Santyl™-Smith & Nephew), trypsin, fibrolysin-desoxyribonuclease; chemical combinations such as Aserbin™ cream; and acids, including but not limited to, salicylic, piruric or phosphoric acids. The debriding composition also preferably includes a solvent or other carrier for the debriding agent, optionally with stabilizers and the like. The debriding composition is preferably at least temporarily in contact with the area of skin to be treated during debridement.

According to preferred embodiments of the present invention, the device preferably comprises the ultrasound source, more preferably connected to an appropriate power source; a spacer for fixing the location of the ultrasound source from the skin to be treated; and a container for containing the acoustic medium, and therefore for acting as an acoustic chamber. Optionally and more preferably, the device further comprises a seal for sealing the lower edges of the container and the skin tissue, and for more preferably acting as an adhesive barrier. The device also more preferably comprises a positioner for holding the device in the proper spatial location, relative to the skin to be treated.

The spacer may optionally and preferably form part of the container, or alternatively, may be a separate component for external support of the ultrasound source.

The container may optionally be rigid or more flexible, and is preferably constructed of any suitable material, such as a plastic or plastic composite or metal sheet for example. The container may optionally include an inlet port for the acoustic medium and/or other liquid and/or gaseous substances and/or a combination thereof, preferably for the optional implementation in which the acoustic medium comprises the debriding composition. The inlet port is also preferred when the debriding composition is either inserted to the container before treatment with the ultrasound source and then removed, or alternatively when the debriding composition is inserted to the container after treatment with the ultrasound source. Of course, both such treatment methods could be employed together, such that the debriding composition is inserted before and/or after treatment with ultrasound. The container also preferably comprises an outlet port, for example to allow exchange of the chamber contents, optionally and more preferably for removing the debriding composition before treatment with ultrasound, and/or (alternatively or additionally) more preferably for removing and/or adding the debriding composition to the container after treatment with ultrasound. The outlet port may also optionally be used to create a vacuum for securing the container to the skin tissue.

Also optionally, such inlet and outlet ports may be used even if the debriding composition is present during treatment with the ultrasound source, since for example the debriding composition may have a different debriding agent and/or formulation at each stage of the treatment, and/or because the debriding composition may optionally be more effective if new debriding composition is inserted after treatment with the ultrasound source. The ports may optionally and preferably be used also for rinsing, flushing or exchanging the fluids inside the chamber (within the container) in any given stage of the procedure.

The seal preferably has sufficient adhesion to prevent undesired displacement of the container (and hence the acoustic chamber) during the treatment. According to a preferred embodiment of the present invention, the seal may optionally comprise a seal body, such as a polyurethane foam element or an inflatable cushion or the like, which may optionally be provided with a bio-compatible adhesive such as an acrylic glue or a thick gel-like substance, to increase the adherence of the seal body to the skin and to seal the container.

The positioner may optionally be the same as the seal or different. According to a preferred embodiment of the present invention, the positioner preferably comprises a plurality of suction ventoses positioned around the container, or a single large ventose that entirely covers the container. Optionally and alternatively, the positioner may comprise a round elastic funnel around the edges of the container, preferably serving as a ventose. Alternatively, the entire container may comprise a suction cup. As a further alternative, mechanical elements such as elastic bandages, straps, or adhesive tapes or the like may optionally be used to position the container. When the positioner is the same as the seal, an adhesive layer under the seal may optionally hold the container in place.

The system according to the present invention preferably comprises the device according to the present invention and the debriding composition, whether such a debriding composition is held in the container, and whether treatment with the debriding composition is performed before, after or during ultrasound treatment, or a combination thereof.

According to optional, alternative embodiments of the present invention, at least one of the ultrasound source and the debriding composition alone is not effective as a treatment, for example by being administered at subtreatment levels. In this case, the combination is preferably such that a synergistic effect is present, such that for example the combination preferably provides greater treatment efficacy than either component alone.

EXAMPLE 1

Illustrative Device and System

The principles and operation of the present invention may be better understood with reference to the drawings and the accompanying description. FIGS. 1-4 show schematic illustrations of various exemplary embodiments of the device according to the present invention, as vertical cross-sections. As used herein, the term "vertical cross-section" refers to a cross-section on a plane which is substantially perpendicular to the surface of the area being treated, and is preferably a symmetry plane of the device. According to preferred but exemplary embodiments of the present invention as shown, the device, or at least a portion thereof, is preferably round in shape, so that each vertical cross-section is the same and FIGS. 1–4 represent any such cross-section.

It should be noted that the device according to the present invention, as described in greater detail below, may optionally feature all components during manufacture and/or before use. Alternatively, such components may be generated at the moment of use by conveniently combining these components. For example, any one or more components may optionally be added to the device to generate the complete device at the moment of use. Preferably, at least one of the ultrasound source and the debriding composition are added to the device at the moment of use.

Figure 1:
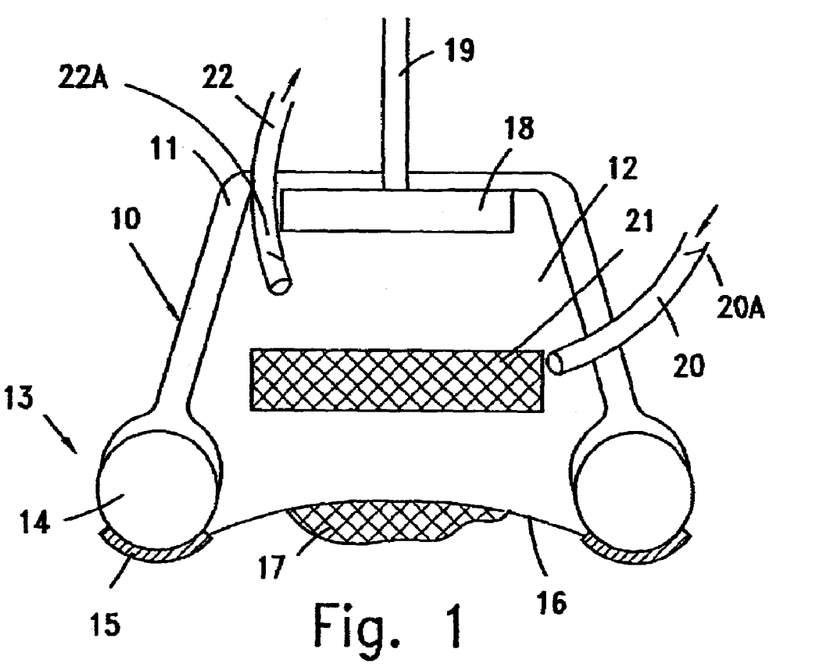
FIG. 1 shows a cross-sectional view of a first exemplary embodiment of a device according to the present invention.

Referring now to the drawings, FIG. 1 shows a device 10 according to the present invention, as a cross-sectional view. Device 10 features a container 11, which is optionally and preferably implemented as a round cup as shown. Container 11 may optionally be constructed of any convenient material, such as metal or plastic, or combination of both for example, and may optionally be rigid or flexible. Container 11 preferably features an acoustic chamber 12 as shown.

At the bottom of container 11 and around the periphery of container 11, a seal 13 is preferably located. Seal 13 more preferably comprises a body 14, optionally and preferably made from elastic foam, and an adhesive layer 15 which preferably contacts the skin of the patient during treatment.

Adhesive layer 15 preferably retains container 11 in the appropriate position with sufficient adhesive strength during treatment.

For the purposes of illustration only and without any intention of being limiting, an area of skin 16 of the patient to be treated is schematically indicated, as is dead tissue 17 at area of skin 16. As shown, device 10 is preferably placed such that container 11 overlays dead tissue 17. The schematic indication of skin 16 and dead tissue 17 is not repeated in the following drawings, but should be considered as obviously implicit, in view of the use of device 10.

Container 11 is preferably closed at the top, and also preferably supports an ultrasound source 18, shown at the top area of acoustic chamber 12. Ultrasound source 18 is preferably connected with conductors 19, passing through an opening (sealed if desired) at the top of container 11, optionally to a controller and preferably to a power source (not shown).

For this embodiment, an inlet conduit 20 is preferably present at container 11, for example, for the introduction of the debriding composition and/or acoustic medium into acoustic chamber 12. It should be noted that the debriding agent, such as the chemical and/or enzymatic debriding agent for example, may optionally be introduced separately into acoustic chamber 12 from some type of solvent or other carrier, and then mixed. Also optionally, the debriding agent may be introduced separately into acoustic chamber 12 from the acoustic medium, and then mixed.

Inlet conduit 20 may optionally and preferably feature a one-way valve 20A. The debriding composition may also optionally be introduced into acoustic chamber 12 as a unit 21.

An outlet 22 may also optionally be provided as shown, for example for evacuating liquid and/or semi-solid material from acoustic chamber 12, and/or for creating a vacuum. Outlet 22 may also optionally and preferably feature a one-way valve 22A.

The distance of ultrasound source 18 from dead tissue 17 is preferably determined by the height of acoustic chamber 12, as ultrasound source 18 is preferably fixed to the inside of the top of container 11.

Figure 2:
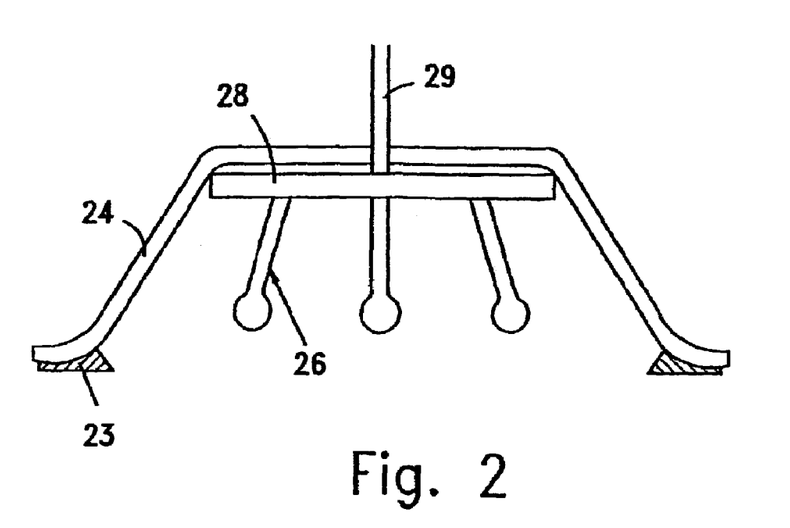
FIG. 2 shows a cross-sectional view of another exemplary embodiment of a portion of the device according to the present invention.

FIG. 2 schematically illustrates another embodiment of a portion of the device according to the present invention, in which a container 24, preferably constructed of a flexible material such as a flexible film for example, is preferably provided with an adhesive barrier 23. An ultrasound source 28 is preferably connected to a power source (not shown) with conductors 29, and is preferably supported by a spacer 26. Spacer 26 may optionally be constructed as a tripod as shown, but alternatively may have any convenient structure. Spacer 26 preferably determines the distance of ultrasound source 28 from the dead tissue to be treated (not shown). The device may optionally be held in place by a mechanical element, such as straps, an elastic dressing or adhesive tape (not shown).

Figure 3:
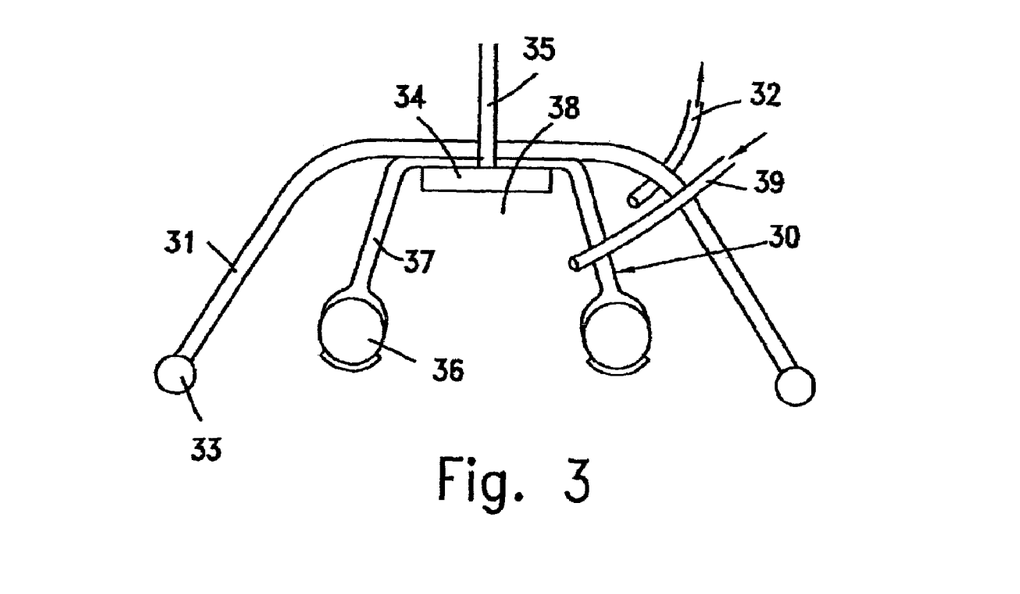
FIG. 3 illustrates another exemplary embodiment of the present invention.

FIG. 3 illustrates another embodiment of the present invention, in which a device 30, generally similar to device 10 of FIG. 1, is held in place with an overlaying element 31. Overlaying element 31 may optionally be an anchoring ventose, and is preferably positioned on the area of skin to be treated by applying a vacuum through an outlet 32. Overlaying element 31 is preferably provided with a seal 33, to permit a vacuum being established therein.

Device 30 also preferably comprises a container 37, including an acoustic chamber 38. Container 37 also preferably supports an ultrasound source 34 provided with conductors 35, and also preferably includes a peripheral seal 36 that may optionally be similar to seal 13 of FIG. 1. Seal 36 preferably isolates acoustic chamber 38 from the compartment between overlaying element 31 and container 37, in which the vacuum is created.

Figure 4:
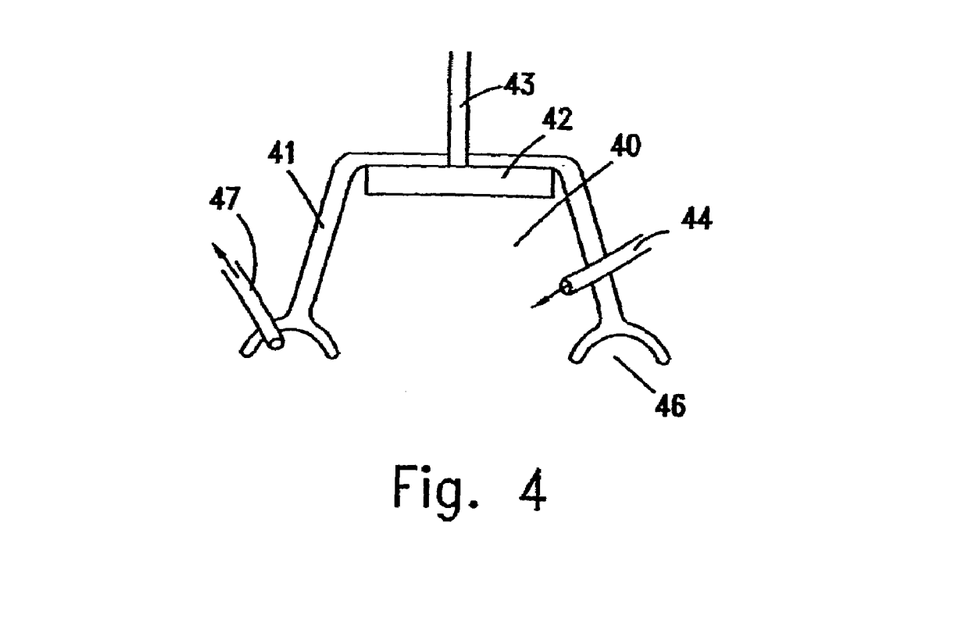
FIG. 4 shows still another exemplary embodiment of the device according to the present invention.

FIG. 4 shows still another embodiment of the device according to the present invention, in which a container 41 includes an acoustic chamber 40. Container 41 retains an ultrasound source 42 with a plurality of conductors 43. An inlet 44 preferably enables a liquid and/or semi-solid material, such as a gel for example, to be introduced to acoustic chamber 40, which as noted above, may optionally contain one or more of the debriding composition or the acoustic medium, or a combination thereof.

An annular cavity 46 preferably provides a seal and a positioner at the periphery of the bottom of container 41, in which a vacuum may optionally be created through outlet 47, so that annular cavity 46 preferably acts as a ventose to secure the device in place.

EXAMPLE 2

In Vivo Studies I

Two in vivo animal studies were performed to illustrate the efficacy of the present invention. This Example and FIGS. 5–9 show pictures of a first in vivo animal study with deep contact burns. It should be noted that the method of treatment described herein is for the purposes of illustration only and is without any intention of being limiting.

The animal experimental model was of a chronic desiccated eschar, considered to be a "worst case scenario" for debridement. The testing animals were young pigs of 20–25 kg of weight. Under general anesthesia and proper monitoring according to proper animal treatment protocols, the bristles along the spine were shaved and the burns were induced. The different test areas were marked and photographed.

A series of deep contact burns, 2 cm in diameter, were left to desiccate for three days, creating a dry eschar, similar to a typical chronic, untreated wound eschar. For treatment, a circular chamber 3 cm in diameter was glued around each area. An ultrasound probe was installed, having a diameter of 1.2 cm that covers half of each eschar site, with its surface covering the lower part of the eschar at a distance of 3 millimeters. At this stage, the chamber was filled with the test material, containing Debridase and saline, or with the control (saline alone). A third control site was a similar eschar treated with hydrated Debridase in an occlusive dressing, without the use of ultrasonic radiation.

Figure 5:
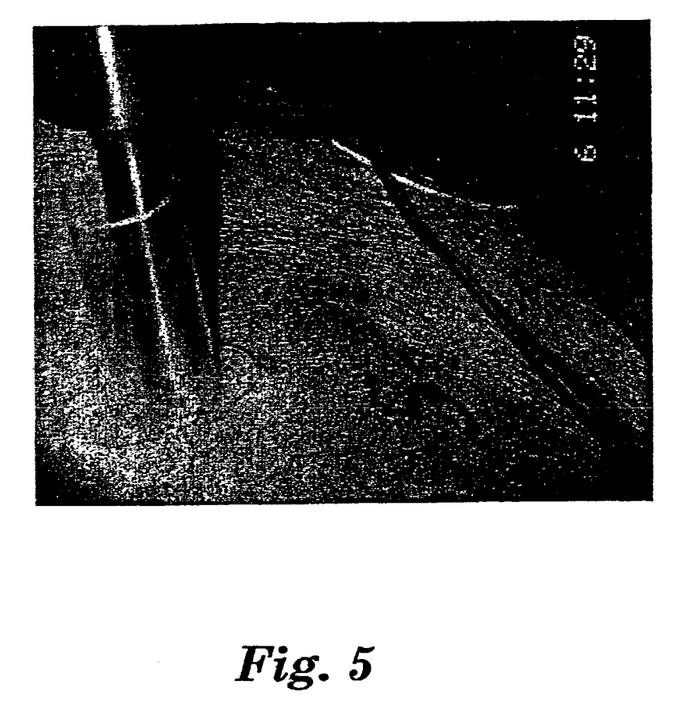
FIG. 5 represents the burn area inside the chamber with the ultrasound probe in place covering the lower part of the eschar.
Figure 6:
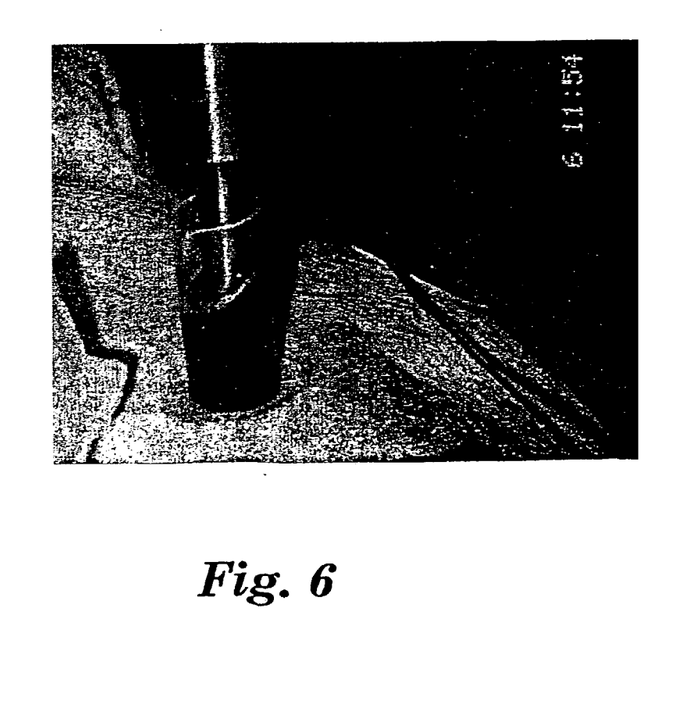
FIG. 6 represents the burn area inside the chamber with the ultrasound probe in place.

FIG. 5 represents the burn area inside the chamber with the ultrasound probe in place covering the lower part of the eschar. FIG. 6 represents the burn area inside the chamber with the ultrasound probe in place, immersed in the dissolved Debridase as the acoustic medium, after 20 minutes of treatment with the ultrasonic radiation. As shown, the Debridase solution is stained with blood.

Figure 7:
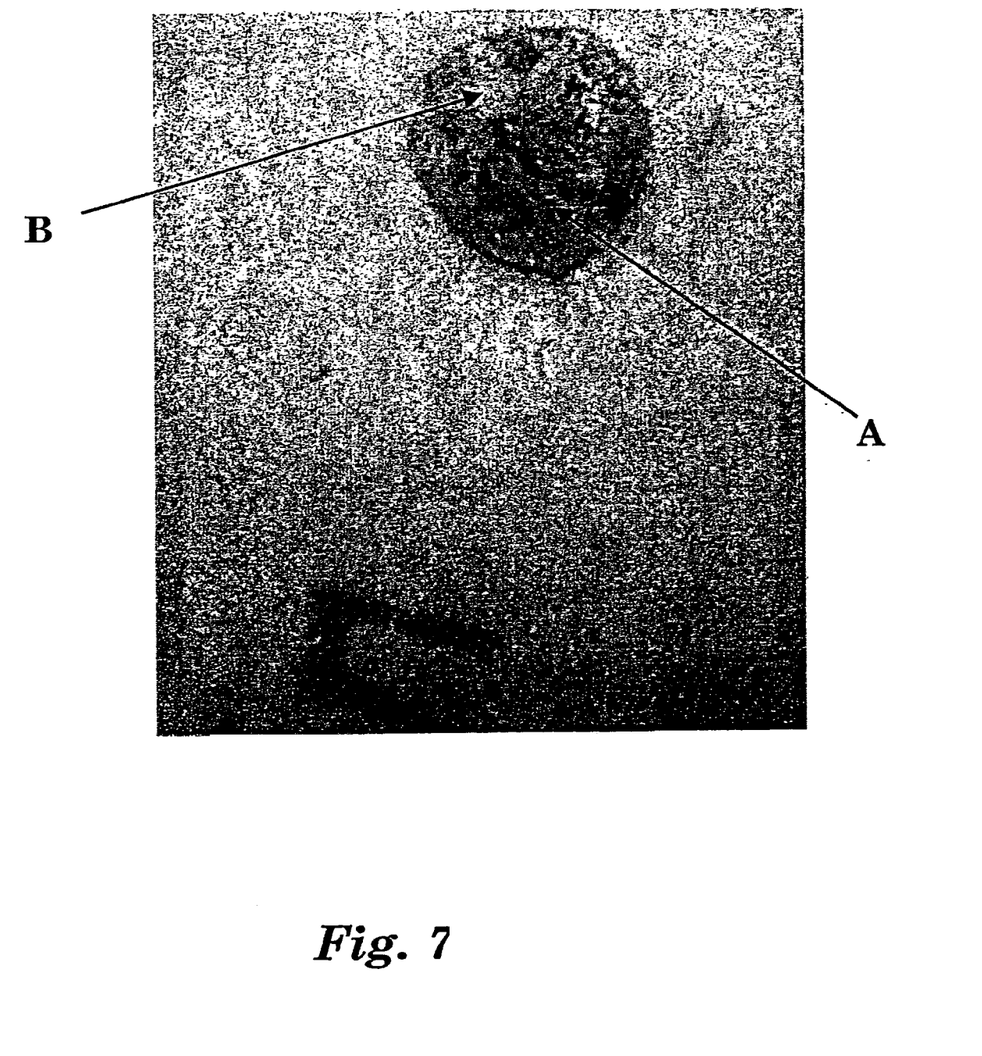
FIG. 7 represents the burn area after 30 minutes of treatment with the Debridase and ultrasonic radiation according to the present invention.

FIG. 7 represents the burn area after 30 minutes of treatment with the Debridase solution and ultrasonic radiation. A completely debrided lower area A can be seen under the ultrasound probe, contrasted by the upper area B, which the probe did not cover and where the eschar remained.

Figure 8:
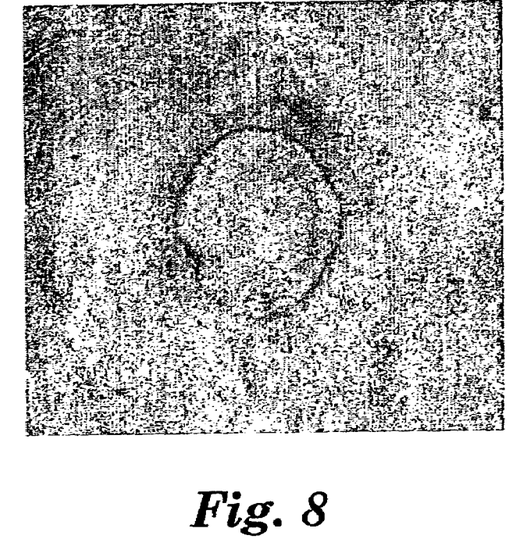
FIG. 8 represents the burn area after 60 minutes of treatment with saline and ultrasonic radiation.

FIG. 8 represents the burn area after 60 minutes of treatment with saline and ultrasonic radiation. As can be seen, the eschar is completely intact without any signs of debridement.

Figure 9:
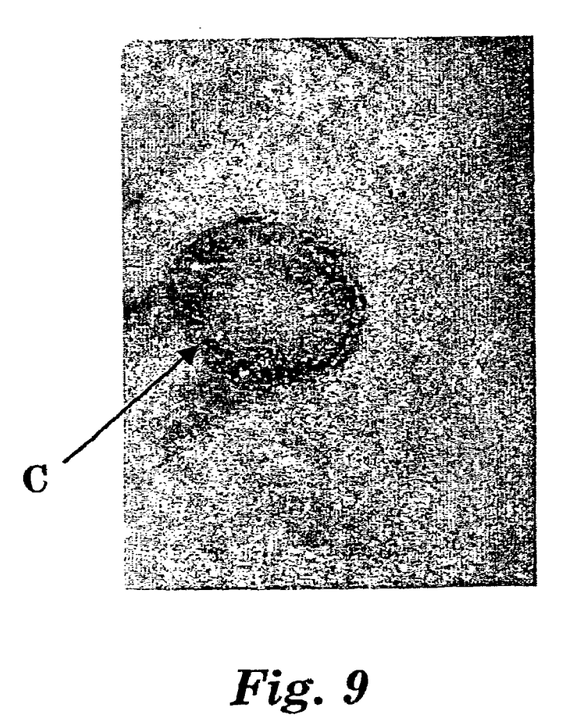
FIG. 9 represents the burn area after 60 minutes of treatment with hydrated Debridase in an occlusive dressing.

FIG. 9 represents the burn area after 60 minutes of treatment with hydrated Debridase in an occlusive dressing.

Some initial debridement can be seen at the edges (marked by arrow C) where the eschar is thinner, but a thick area of eschar remains in the center.

The above animal study showed that the use of a debriding agent/composition (represented by Debridase) alone produced a limited debridement as expected. The use of ultrasonic radiation alone without any debriding agent did not have any debriding effect. However, the combination of the debriding composition and locally applied ultrasonic radiation produced a significant debridement, with a greater overall effect than the debriding agent/composition alone, and also more rapidly than the debriding agent/composition alone.

EXAMPLE 3

In Vivo Studies II

For the second study, the ischemic flap model of inflicting chronic eschar was chosen as most closely imitating the actual clinical behavior of eschar in human chronic wound patients. The model is obtained by incising the skin of young domestic pigs, approx. 20–25 kg as described above, to create long and narrow flaps (3×7 cm) where, due to the very negative base/length ratio, the ends of the flaps are ischemic and will necrotize. This necrotizing course follows exactly the natural course of necrotizing ischemic soft tissue in humans.

Figure 10:
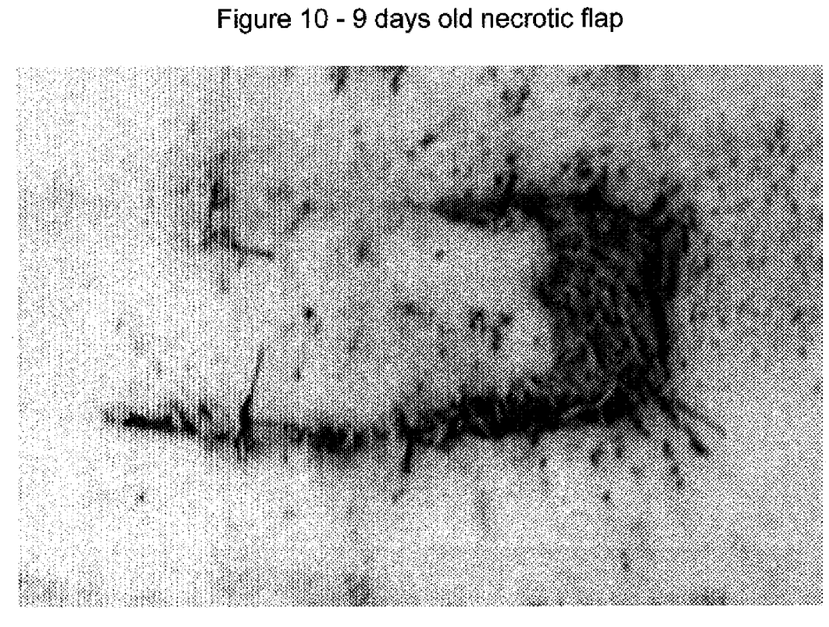
FIG. 10 shows a 9 day old necrotic flap before treatment according to the present invention.

The skin was allowed to be ischemic for variable lengths of time before treatment. It was found that leaving the flaps for 6 days causes a dry, black eschar in the ischemic distal area to form, while leaving the flaps for 9 days causes the eschar to start to slough at its connection to the viable tissue. FIG. 10 shows a 9 day old necrotic flap before treatment according to the present invention.

Also, the efficacy of Debridase was tested after exposure to ultrasonic radiation at 20 kHz 10W for 30 minutes in order to establish its activity after such exposure.

The 6 days model of ischemia was used with the formal 4 hour Debridase in hydrating gel, with and without ultrasonic radiation. The 9 days model of ischemia was used in combinations with ultrasonic radiation and Debridase. The ultrasound source featured the previous probes, with an output of 20 kHz and 10 W/cm$^2$ or 57 kHz and 8W/cm$^2$. Ultrasound was also used as a pretreatment primer before application of the Debridase, together with the Debridase (gel replaced by saline) and in conjunction with SLS (surface active compounds).

For the 9 days model of ischemia, the following combinations were used: control treatment of 4 hours with Debridase in water; a first application of ultrasonic radiation at 20 kHz/10W/cm$^2$ with Debridase in water (DWD) for 30 minutes with a second application of ultrasonic radiation at 20 kHz/10W/cm$^2$ with Debridase in gel for 30 minutes, with free-hand (manual) use of the ultrasound probe on a Debridase in hydrating gel, such that the probe was used without an acoustic chamber and with the ultrasound probe manually held over the eschar; a pretreatment for five minutes with ultrasonic radiation and SLS, followed by 4 hours Debridase in hydrating gel; a pretreatment for five minutes with ultrasonic radiation and then 4 hours Debridase in hydrating gel; and treatment with Debridase in water and SLS for 4 hours.

RESULTS

The Model

The 6 days model seems to represent the "fresh" chronic eschar that is still attached to the living tissue. The eschar is not decomposed (necrotic) as yet and is not completely dry.

The 9 days model represents the more chronic, contaminated eschar that starts to macerate. The main body of these eschars is a hard, dry, black mass but along its edges the maceration process begins. The transition line between the eschar and the living tissue is well defined and in some points a furrow starts to form indicating the level of the future sloughing.

Debridement

Debridase in water that was exposed to ultrasonic radiation proved to be effective, similar to the combination of ultrasonic radiation with the previously tested composition of Debridase in hydrating gel.

The combination of ultrasound and Debridase proved to be effective in debridement of the standard burn model eschar.

The first set of debridement trials were performed with the 6 days model of ischemia and the formal 4 hours Debridase in hydrating gel (without ultrasound). In all 5 areas, a beginning of debridement of the eschar could be seen in the areas that were less desiccated and from the edges where the Debridase in hydrating gel had contact with the dermis. At the edges of the living tissue, which featured an inflammatory reaction, the surface was debrided and raw tissue was exposed. None of the five eschars was debrided completely in one single Debridase in hydrating gel application (without ultrasound).

The second set of debridement trials were performed with the 9 days model of ischemia. Different combinations were tested as described above. The results were as follows. For the treatment with ultrasonic radiation and 4 hours Debridase in hydrating gel, the healthy tissue edges were cleaned, with nearly complete separation of the eschar without much effect on the eschar itself. Using ultrasonic radiation together with Debridase in water provided similar results as 4 hours Debridase in hydrating gel treatment.

Figure 11:
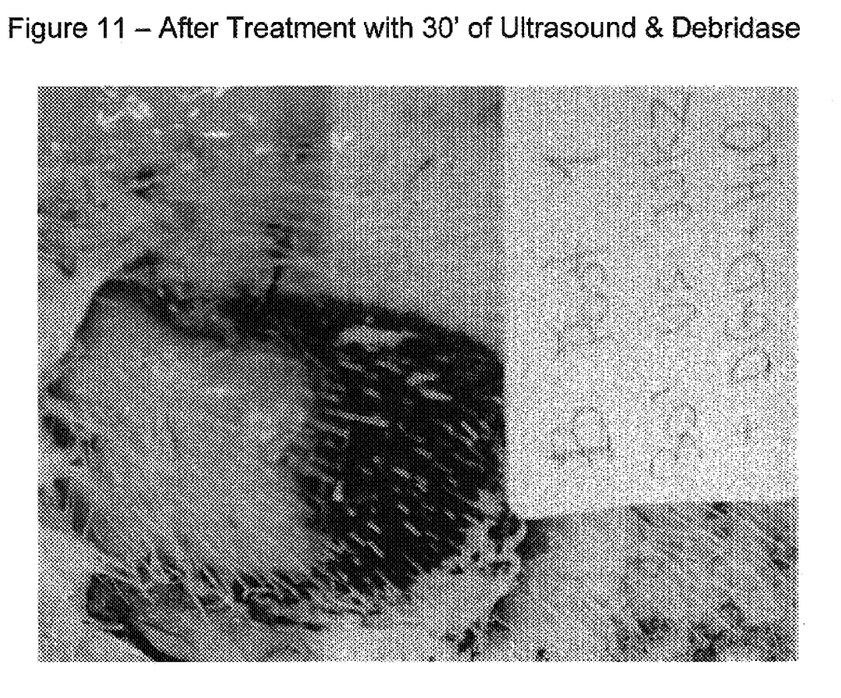
FIG. 11 shows a 9 day old necrotic flap after 30 minutes of treatment with ultrasound and Debridase according to the present invention.
Figure 12:
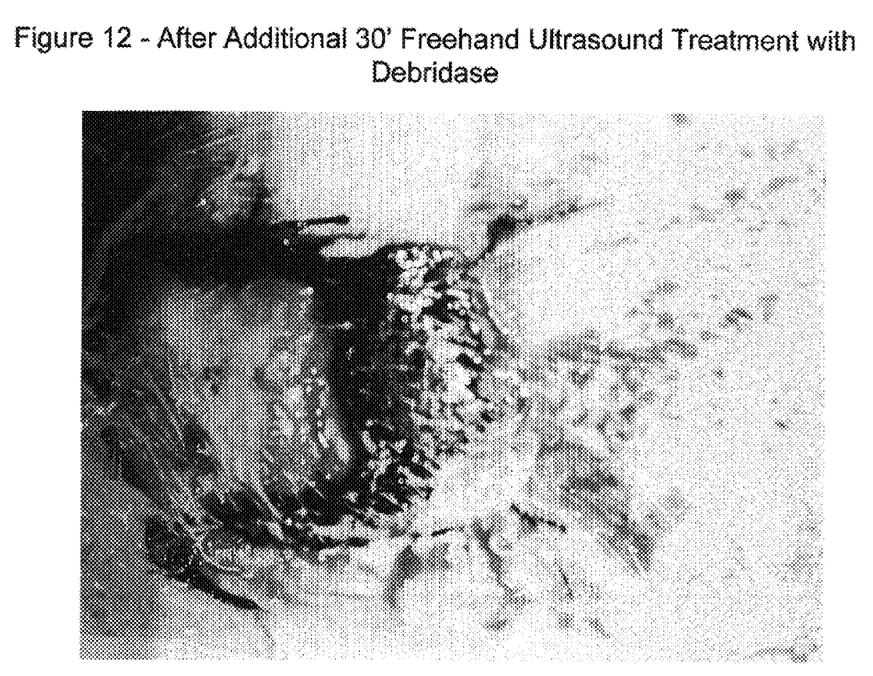
FIG. 12 shows the flap after an additional 30 minutes of treatment with ultrasound (free hand) and Debridase according to the present invention.
Figure 13:
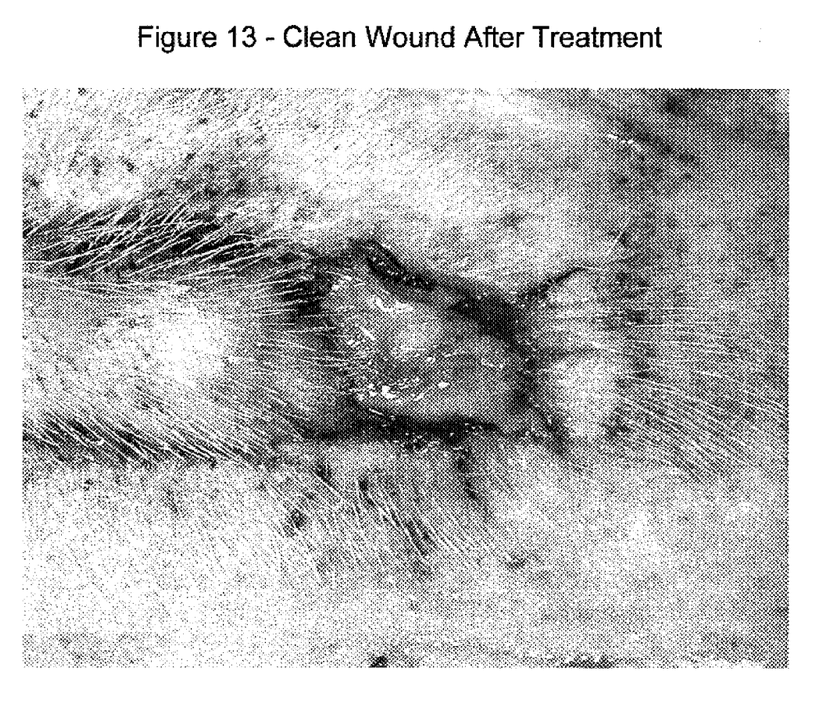
FIG. 13 shows that after the wound is wiped (after the treatment according to the present invention performed with regard to FIGS. 11 and 12), the wound is entirely clean.

FIG. 11 shows a 9 day old necrotic flap after 30 minutes of treatment with ultrasound and Debridase. FIG. 12 shows the flap after an additional 30 minutes of treatment with ultrasound (free hand) and Debridase. FIG. 13 shows that after the wound is wiped (after the treatment according to the present invention performed with regard to FIGS. 11 and 12), the wound is entirely clean.

As shown in these Figures, the additional free-hand use of the ultrasound probe on Debridase in hydrating gel without a chamber showed improved cleaning of the living edges of skin tissue. Wiping the area to remove the gel caused the entire eschar to be removed together with a "tail" of a necrotic subdermal tissue attached to the fill thickness eschar. The tissue that was left seemed to be clean.

Pretreatment with ultrasound for five minutes with SLS, followed by 4 hours Debridase in hydrating gel provided some cleaning at the edges of the skin, and was similar to treatment with Debridase in hydrating gel alone.

Pretreatment with ultrasound for five minutes followed by 4 hours Debridase in hydrating gel was similar to treatment with Debridase in hydrating gel alone. Due to technical difficulties in keeping the liquid Debridase plus water in the chamber, it was replaced after 30' with Debridase in hydrating gel. Treatment with Debridase in water plus SLS for 4 hours was similar to treatment with Debridase in hydrating gel alone.

CONCLUSIONS

Debridase remains effective after being exposed to ultrasonic radiation, and the combination of Debridase together with ultrasonic radiation treatment is useful, including with simultaneous application. Currently, pretreatment with ultrasound and/or SLS before application of Debridase does not show any additional benefit, but this may be due to the particular combination selected.

EXAMPLE 4

Method of Treatment

The method of treatment according to the present invention preferably comprises contacting the skin of a patient with a debriding composition, and applying ultrasonic radiation to the skin. These processes may optionally and preferably be performed in any order, including simultaneously. More preferably, these processes are performed repeatedly for at least one repetition, and more preferably a plurality of repetitions. Optionally, only one of the two processes may be performed for a particular repetition. As previously described, the method of the present invention is useful for debridement, preferably for removal of dead skin tissue.

The duration of treatment, the intensity of the ultrasonic radiation and the concentration and overall amount of the debriding agent in the composition, as well as the amount of the composition itself may optionally and preferably be each determined individually, for example by the attending physician. The debriding composition, along with the overall treatment method, is preferably used in a therapeutically effective amount.

As used herein, the term "therapeutically effective amount" means the total amount of each active component of the pharmaceutical composition or method that is sufficient to show a meaningful patient benefit, ie., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of the present invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the overall seriousness of the disease or disorder, and should be decided according to the judgment of the practitioner and each patient's circumstances.

The duration of treatment according to the present invention will vary, depending on the severity of the skin condition being treated and the condition and potential idiosyncratic response of each individual patient.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system for debridement of an area of eschar, comprising:
   (a) a device comprising an ultrasound source for delivering ultrasound radiation having a debriding effect on eschar, a spacer for maintaining the ultrasound source at a distance from the area of eschar and a container coupled to the ultrasound source, said container being adapted to be placed over the area of eschar, said container containing an acoustic medium for enabling the area of eschar to be exposed to ultrasonic radiation from said ultrasound source; and
   (b) a debriding composition for use in combination with said ultrasonic radiation and being in contact at least temporarily with said area of eschar, wherein the debriding composition comprises at least one enzymatic debriding agent.

2. The system of claim 1, wherein said acoustic medium includes said debriding composition.

3. The system of claim 2, wherein said container further comprises an opening for enabling said debriding composition to contact said area of skin to be debrided.

4. The system of claim 3, wherein said container further comprises a peripheral seal for sealing said opening against said area of skin to be debrided.

5. The system of claim 3, further comprising an inlet in said container for inserting said debriding composition.

6. The system of claim 5, further comprising an outlet in said container for removing said debriding composition.

7. The system of claim 5, further comprising an outlet in said container for creating a vacuum for sealing said opening against said area of skin.

8. The system of claim 1, wherein said container further comprises an opening for being placed against said area of skin to be debrided, and also further comprises an inlet, such that said debriding composition may be inserted into said container before, during or after treatment with said ultrasonic radiation.

9. The system of claim 8, wherein said container further comprises an outlet for removing at least one of said acoustic medium and said debriding composition.

10. The system of claim 8, wherein said container further comprises a peripheral seal for sealing said opening against said area of skin to be debrided.

11. The system of claim 1, wherein said ultrasound source comprises a piezoelectric ultrasound source unit.

12. The system of claim 1, wherein said spacer is combined with said container.

13. The system of claim 1, wherein said debriding composition further comprises at least one chemical agent.

14. The system of claim 1, wherein said debriding composition further comprises at least one of a liquid and a semi-solid carrier.

15. The system of claim 1, wherein said debriding composition further comprises a stabilizer.

16. The system of claim 1, wherein said debriding composition comprises a vegetable preparation.

17. The system of claim 16, wherein said vegetable preparation comprises a bromelain derivative.

18. The system of claim 17, wherein said bromelain derivative comprises Debridase.

19. A method for debridement of an area of dead skin tissue comprising:
- contacting the area of dead skin tissue with a debriding composition, the debriding composition comprising at least one enzymatic debriding agent; and
- applying ultrasonic radiation having a debriding effect on dead skin tissue to the area of dead skin tissue;
- wherein said contacting and said applying are performed in any order and said ultrasonic radiation enhances debridement of the dead skin tissue by the debriding composition.

20. The method of claim 19, wherein said applying and said contacting are performed concurrently.

21. The method of claim 19, wherein said applying is performed before said contacting.

22. The method of claim 19, wherein said contacting is performed before said applying.

23. The method of claim 19, wherein said debriding composition further comprises at least one chemical debriding agent.

24. The method of claim 19, wherein said debriding composition further comprises at least one of a liquid and a semi-solid carrier.

25. The method of claim 19, wherein said debriding composition further comprises a stabilizer.

26. The method of claim 19, wherein said debriding composition comprises a vegetable preparation.

27. The method of claim 26, wherein said vegetable preparation comprises a bromelain derivative.

28. The method of claim 27, wherein said bromelain derivative comprises Debridase.

29. A system for debridement of dead skin tissue, comprising:
- (a) a device comprising an ultrasound source for delivering ultrasound radiation having a debriding effect on dead skin tissue, a spacer for maintaining the ultrasound source at a distance from the area of dead skin tissue and an acoustic medium for enabling the area of dead skin tissue to be exposed to ultrasonic radiation from the ultrasound source, wherein said ultrasound source is placed in contact with said acoustic medium manually; and
- (b) a debriding composition for use in combination with said ultrasonic radiation and being in contact, at least temporarily, with the area of dead skin tissue, wherein the debriding composition comprises at least one enzymatic debriding agent.

30. The system of claim 29, wherein said acoustic medium includes said debriding composition.

31. The system of claim 29, wherein said debriding composition further comprises at least one chemical debriding agent.

32. The system of claim 29, wherein said debriding composition further comprises at least one of a liquid and a semi-solid carrier.

33. The system of claim 32, wherein said debriding composition further comprises a stabilizer.

34. The system of claim 29, wherein said debriding composition comprises a vegetable preparation.

35. The system of claim 34, wherein said vegetable preparation comprises a bromelain derivative.

36. The system of claim 35, wherein said bromelain derivative comprises Debridase.

\* \* \* \* \*